US005461055A

United States Patent [19]

Cooper et al.

[11] Patent Number: 5,461,055

[45] Date of Patent: Oct. 24, 1995

[54] NIKKOMYCIN ANALOGS

[75] Inventors: Alan B. Cooper, West Caldwell; Anil K. Saksena, Upper Montclair; Raymond Lovey, West Caldwell; Viyyoor Girijavallabhan, Parsippany; Ashit Ganguly, Upper Montclair, all of N.J.

[73] Assignee: Schering Corporation, Kenilworth, N.J.

[21] Appl. No.: 253,640

[22] Filed: Jun. 3, 1994

Related U.S. Application Data

[60] Division of Ser. No. 900,712, Jun. 18, 1992, Pat. No. 5,346,898, which is a continuation-in-part of Ser. No. 747, 554, Aug. 20, 1991, abandoned.

[51] Int. Cl.[6] .................... A61K 31/505; C07D 239/10; C07D 215/00

[52] U.S. Cl. .................... 514/269; 514/274; 514/314; 544/310; 544/363; 546/153; 546/155; 546/175; 546/180

[58] Field of Search .................... 514/19, 43, 50, 514/252, 269, 274, 341, 359, 383, 396, 397, 314; 536/23, 24, 28.7, 28.8; 544/310, 311, 312, 372, 373, 374, 405, 408, 363; 546/276, 277, 278, 153, 155, 175, 180; 548/262.2, 266.4, 312.1, 316.4, 317.1, 335.1, 346.1, 350.1

[56] References Cited

U.S. PATENT DOCUMENTS

| | | | |
|---|---|---|---|
| 4,158,608 | 6/1979 | Dahn et al. | 514/50 |
| 4,315,922 | 2/1982 | Hagenmaier et al. | 424/181 |
| 4,552,954 | 11/1985 | Moeschler et al. | 536/24 |
| 4,585,761 | 4/1986 | Zahner et al. | 514/43 |
| 4,914,087 | 4/1990 | Hector et al. | 514/50 |
| 5,236,900 | 8/1993 | Cooper et al. | 514/19 |
| 5,238,926 | 8/1993 | Cooper et al. | 514/50 |

OTHER PUBLICATIONS

Antimicrobial Agents and Chemotherapy, Apr., 1990 pp. 587–593.

Kingsbury et al., J. Org. Chem. 1986, 51, 2307–2314.

J. Org. Chem., 1990, 55 pp. 3772–3787, Garner et al.

Naider et al., vol. 24, 1983, Antimicrobial Agents and Chemotherapy.

Tetrahedron Letters, vol. 30, 38, 5065–5068, Garner et al, 1989.

CA 106(23):192579X, 1987.

Becker et al, J. Med. Chem., 1986, 29, 802–809.

*J. Med Chem,* 1988, 31, pp. 650–656, Khare et al.

JACS, Jul. 28, 1971, pp. 3812–3813.

New Synthetic Polyoxin Analogs For Chitin Synthesis Inhibition, Smith et al, Chitin Nat. Technol. 3rd, 1985, pp. 197–202.

*Primary Examiner*—Yogendra N. Gupta

*Attorney, Agent, or Firm*—Eric S. Dicker; John J. Maitner; Boxer Matthew

[57] ABSTRACT

Compounds of the formula

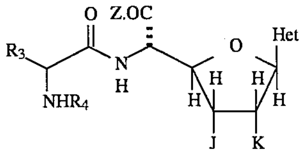

I wherein $R_3$, $R_4$, J, K, Z, and Het are as set forth herein are described.

The compounds of formula I are useful as agents in the treatment of fungal infections.

9 Claims, No Drawings

NIKKOMYCIN ANALOGS
This is a division of Ser. No. 07/900,712, filed Jun. 18, 1992, now U.S. Pat. No. 5,346,898; which in turn is a continuation-in-part of Ser. No. 07/747,554 filed Aug. 20, 1991, now abandoned.
SUMMARY OF THE INVENTION
The invention relates to compounds of the formula
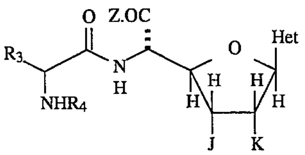
I
or pharmaceutically acceptable salts thereof, wherein Het is
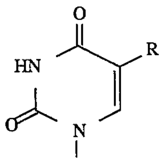
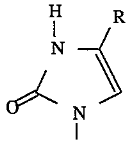
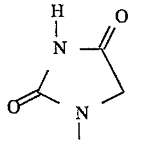
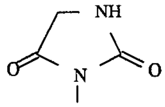
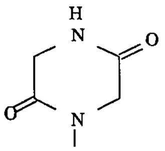
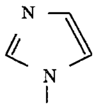
or
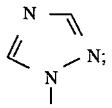
R is H, COOH; $C_1$–$C_{12}$ alkyl; CHO; CN; $CH_2OH$; or $CONH_2$;
wherein $R_3$ is
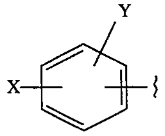
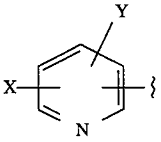
or
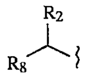
wherein $R_8$ is
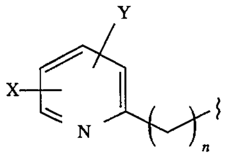
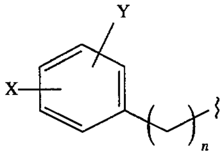
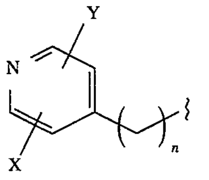
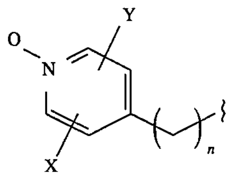
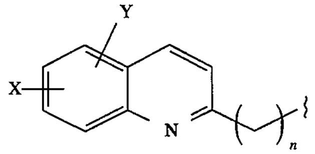
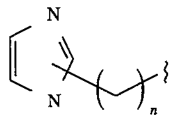
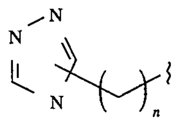
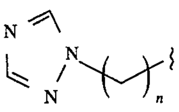
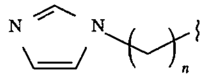
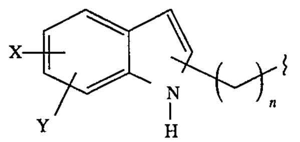
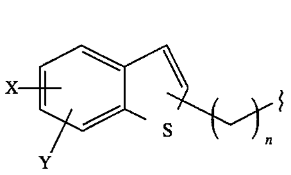
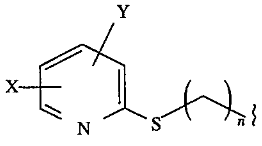
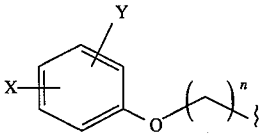
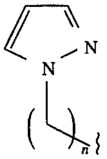
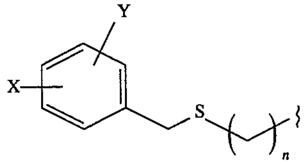

-continued

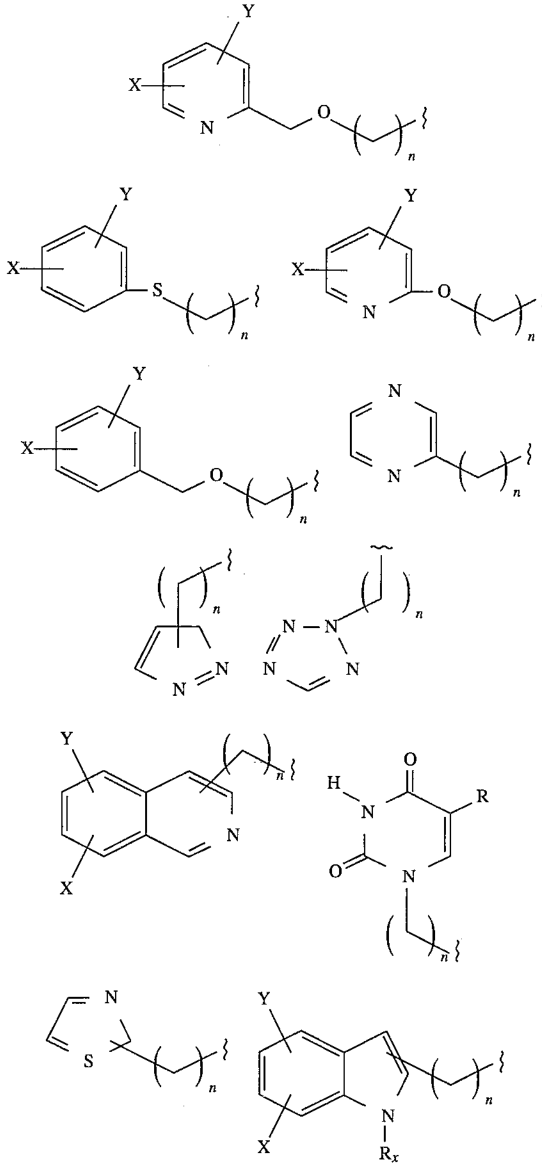

$R_2$ is H; OH; F; $C_1$–$C_6$ alkoxy; alkyl; SH; S-alkyl; or $SO_2$-alkyl;

$R_4$ is H; a natural amino acid attached by a peptide bond; or a metabolizable group;

$R_x$ is $C_1$–$C_{12}$ alkyl;

J is OH, H, Br, Cl, or F;

K is OH, H, Br, Cl, or F;

X and Y are the same or different and are independently selected from the group consisting of H; OH; O—$C_1$–$C_{14}$ alkyl; F; Cl; Br; I; $NO_2$, and alkyl;

Z is $R_5NR_6$;

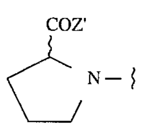

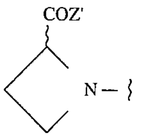

or

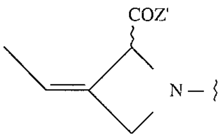

wherein

Z' is $R_5NR_6$, $R_5$ is H, a saturated or unsaturated $C_6$–$C_{18}$ aliphatic side chain; or a hydroxylated $C_6$–$C_{18}$ aliphatic side chain;

$R_6$ is H; OH; benzyl; substituted benzyl; O-benzyl; O-aryl; O—$C_4$–$C_{14}$ alkyl; $C_1$–$C_{12}$ alkyl; phenyl; substituted phenyl; or CO—$R_7$; and $R_7$ is H, $C_1$–$C_{16}$ alkyl, aryl or alkylaryl; and n is an integer from 0 to 16.

Preferred are compounds of formula I wherein Het is uracil.

Also preferred are compounds of formula I wherein $R_4$ is H.

Preferred are compounds of formula I where J and K are both OH.

Preferred are compounds of formula I wherein $R_5$ is a $C_{10}$–$C_{18}$ saturated aliphatic side chain:

Most preferred are compounds of formula I wherein $R_5$ is a straight-chained —$(CH_2)_{11}CH_3$.

Preferred are compounds of formula I wherein the stereochemistry at the 2" position is S according to Cahn, Ingold, Prelog rules of stereochemistry or L according to the natural stereochemistry of amino acids. Also encompassed by formula I are compounds of the opposite stereochemistry, that is, wherein 2" position has the R or D configuration.

Formula I is reproduced just below to show where the 2" and 1" positions are.

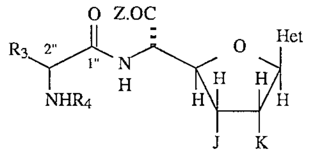

I

Alkyl denotes straight or branched hydrocarbon chains, which contain from 1 to 20 carbon atoms. Representative examples include methyl, ethyl, propyl, decyl, dodecyl and the like. Alternatively, the number of carbon atoms in a particular alkyl may be specified. For example, $C_1$–$C_6$ alkyl refers to an alkyl which may have one to six carbon atoms.

Alkoxy denotes O-alkyl wherein alkyl is as described above.

As used herein the term UR denotes uracil. The structural formula for the uracil moiety is

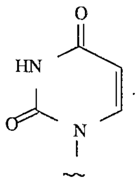

The term UPOC denotes uracil polyoxin C. The structural formula for UPOC is

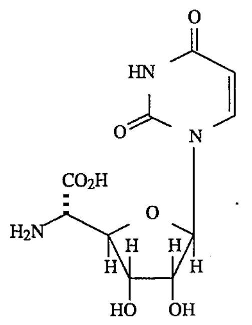

The term natural amino acid denotes the following amino acids; glycine and the following which have an L-configuration: valine, leucine, isoleucine, serine, aspartic acid, asparagine, glutamic acid, histidine, alanine, proline, phenylalanine, tryptophan, methionine, threonine, cysteine, tyrosine, glutamine, lysine and arginine which are also referred to respectively by the following abbreviations:

Gly, Val, Leu, Ile, Ser, Asp, Asn, Glu, His, Ala, Pro, Phe, Trp, Met, Thr, Cys, Tyr, Gln, Lys and Arg.

The term metabolizable group denotes any group which under metabolizable conditions (that is, when subjected to metabolic enzymes and the like) will be cleaved off. An example is

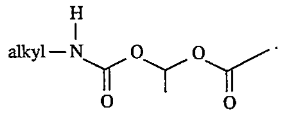

The term saturated aliphatic side chain denotes a straight or branched saturated side chain containing only carbons and hydrogen. The saturated aliphatic side chain may contain up to 20 carbon atoms. Alternatively, the number of carbon atoms in an saturated aliphatic side chain may be specified. For example, a saturated $C_6$–$C_{18}$ aliphatic side chain denotes a saturated aliphatic side chain having from 6 to 18 carbon atoms. The saturated aliphatic side chain may contain within the chain up to three of any combination of the heteroatoms O, S, or N, with the proviso that such heteroatoms cannot be adjacent to each other in the chain. The saturated aliphatic side chain may also have a carboxyalkyl functionality.

The term unsaturated aliphatic side chain denotes a straight or branched aliphatic side chain containing up to three double or triple bonds or any combination thereof. For example an unsaturated aliphatic side chain may contain three double bonds, two double bonds and one triple bond, one double bond and two triple bonds, or three triple bonds. The unsaturated aliphatic side chain may contain up to 20 carbon atoms. Alternatively, the number of carbon atoms in an unsaturated aliphatic side chain may be specified. For example, a unsaturated $C_6$–$C_{18}$ aliphatic side chain denotes an unsaturated aliphatic side chain having from 6 to 18 carbon atoms. The unsaturated aliphatic side chain may contain within the chain up to three of any combination of the heteroatoms O, S, or N, with the proviso that such heteroatoms cannot be adjacent to each other in the chain. The unsaturated aliphatic side chain may also have a carboxyalkyl functionality.

A hydroxylated aliphatic side chain denotes a saturated or unsaturated, straight or branched aliphatic side chain as described above, wherein up to 3 hydrogens are replaced by OH. The hydroxylated aliphatic side chain may contain up to 20 carbon atoms. Alternatively, the number of carbon atoms in an hydroxylated aliphatic side chain may be specified. For example, a hydroxylated $C_6$–$C_{18}$ aliphatic side chain denotes an hydroxylated aliphatic side chain having from 6 to 18 carbon atoms. The hydroxylated aliphatic side chain may contain within the chain up to three of any combination of the heteroatoms O, S, or N, with the proviso that such heteroatoms cannot be adjacent to each other in the chain. The hydroxylated aliphatic side chain may also have a carboxyalkyl functionality.

Aryl denotes a mono or bi-cyclic aromatic system. Examples of preferred aryl groups include those having from 6 to 14 carbon atoms. Representative examples include phenyl, 1-naphthyl, 2-naphthyl, and indanyl. The aryl group may contain additional substituents selected from the group consisting of: halogen atoms (e.g. Cl, Br, F and/or I), alkoxy, alkyl, and amino.

Alkylaryl denotes an aryl as described herein, wherein one of the hydrogens of the aryl is substituted by an alkyl as described herein.

A substituted phenyl refers to a phenyl bearing up to three substituents independently selected from the group consisting of —S-alkyl, —S—H, amino, $NO_2$, and O-alkyl; and up to five substituents independently selected from the group consisting of F, Cl, I, Br, alkyl, and OH.

A substituted benzyl refers to a benzyl with the phenyl portion thereof bearing up to three substituents independently selected from the group consisting of —S-alkyl, —S—H, amino, $NO_2$, and O-alkyl; and up to five substituents independently selected from the group consisting of F, Cl, I, Br, alkyl, and OH.

As used herein, a boldfaced bond, denotes a bond which comes up out of the plane of the page. A dashed bond, denotes a bond which comes down below of the plane of the page. A curved bond, denotes a racemic mixture.

Exemplary compounds of the invention include:

The invention relates to compounds of the formula

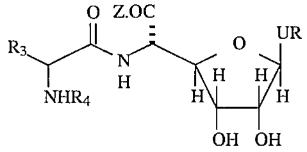
| No. | 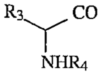 | Z.OC |
| --- | --- | --- |
| 1. | 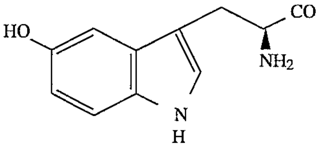 | $CONH(CH_2)_3CH_3$ |
| 2. | 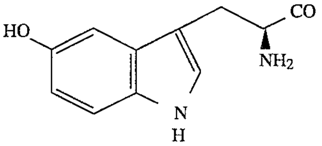 | $CONH(CH_2)_7CH_3$ |
| 3. | 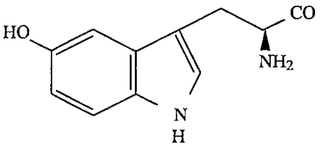 | $CONH(CH_2)_{11}CH_3$ |
| 4. | 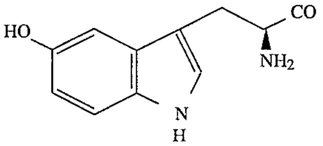 | $CONH(CH_2)_{17}CH_3$ |
| 5. | 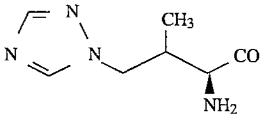 | $CONH(CH_2)_{11}CH_3$ isomer 1 |
| 6. | 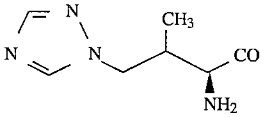 | $CONH(CH_2)_{11}CH_3$ isomer 2 |
| 7. | 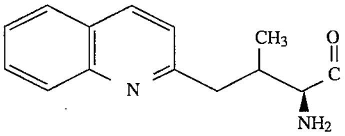 | $CONH(CH_2)_{11}CH_3$ isomer 1 |
| 8. | 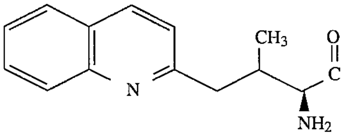 | $CONH(CH_2)_{11}CH_3$ isomer 2 |
| 9. | 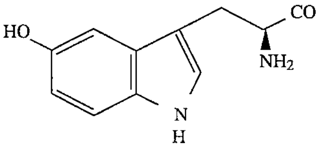 | $CONH(CH_2)_{13}CH_3$ |

-continued
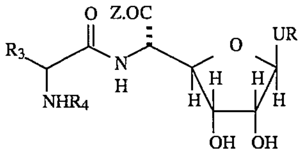
| No. | 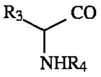 | Z.OC |
|---|---|---|
| 10. | 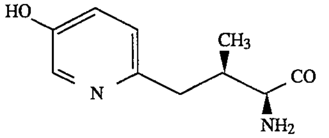 | $CONH(CH_2)_{11}CH_3$ |
| 11. | 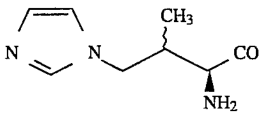 | $CONH(CH_2)_{11}CH_3$ |
| 12. | 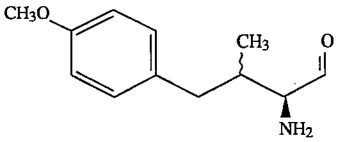 | $CONH(CH_2)_{11}CH_3$ |
| 13. | 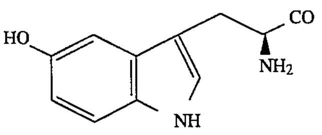 | $CONH(CH_2)_9CH_3$ |
| 14. | 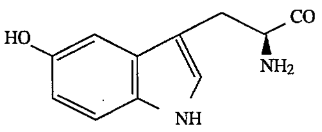 | $CON(OBZL)(CH_2)_{11}CH_3$ |
| 15. | 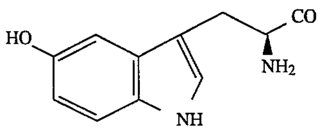 | 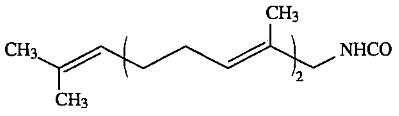 |
| 16. | 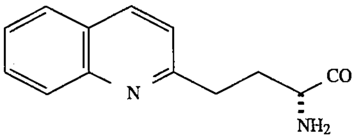 | $CONH(CH_2)_{11}CH_3$ |
| 17. | 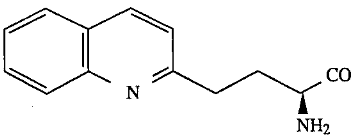 | $CONH(CH_2)_{11}CH_3$ |
| 18. | 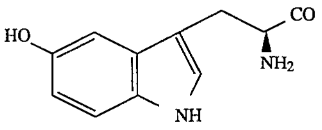 | $CON(OH)(CH_2)_{11}CH_3$ |
| 19. | 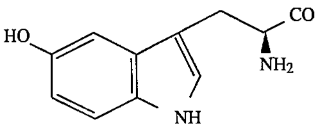 | 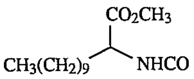 |

-continued

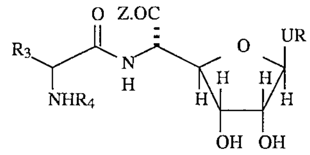

| No. | 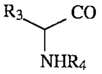 | Z.OC |
|---|---|---|
| 20. | 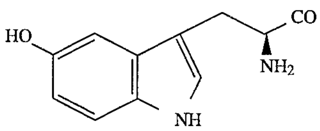 | 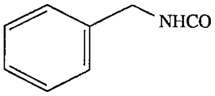 |
| 21. | 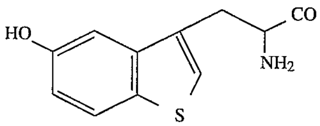 | $CONH(CH_2)_{11}CH_3$ isomer 1 |
| 22. | 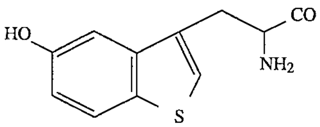 | $CONH(CH_2)_{11}CH_3$ isomer 2 |
| 23. | 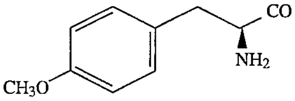 | $CONH(CH_2)_{11}CH_3$ |
| 24. | 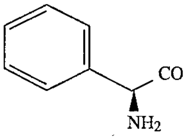 | $CONH(CH_2)_{11}CH_3$ |
| 25. | 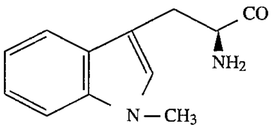 | $CONH(CH_2)_{11}CH_3$ |

In the above table and throughout the specification, OBZL denotes O-benzyl.

Preferred compounds of the invention are: t,150

The most preferred compound of the invention is

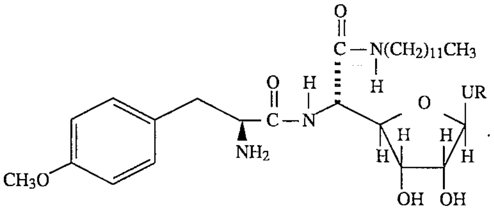

The invention also relates to a pharmaceutical composition which comprises a compound of formula I in combination with a pharmaceutically acceptable carder material.

The invention also relates to a method for treating fungi which comprises administering to a mammal in need of such treatment an anti-fungally effective amount of a compound of formula I: for such purpose.

DETAILED DESCRIPTION OF THE INVENTION

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization or HPLC (high performance liquid chromatography).

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

The compounds of formula I form pharmaceutically acceptable salts. The preferred pharmaceutically acceptable salts are nontoxic acid addition salts formed by adding to a compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, paratoluenesulfonic, methane sulfonic, citric, maleic, fumaric, succinic and the like, respectively.

The compounds of formula I above may be administered in compositions that also contain other anti-fungal agents. The compounds of formula I above may also be administered at the same time that other anti-fungal agents are being administered.

The compounds of formula I above may be prepared by the methods described below with reference to Schemes 1 and 2 wherein $R_3$, $R_4$, Het, J, K and Z are as described above unless otherwise indicated. t,180

$R_{10}$ is an N-blocked natural amino acid, or an N-blocked metabolizable group; or a nitrogen protecting group such as tert-butoxycarbonyl or benzyloxycarbonyl.

As used herein Osu denotes N-oxysuccinimide, HOsu denotes N-hydroxysuccinimide, DCC denotes 1,3-dicyclohexylcarbodiimide, HObt denotes N-hydroxybenztriole, DMF denotes N,N-dimethylformamide, THF denotes tetrahydrofuran.

The compounds of formulas II and IV are known, can be prepared in accordance with known methods, or else their preparation is described herein.

A compound of formula II may be converted to the corresponding N-oxysuccinimide ester of formula III thereof by reaction with N-hydroxysuccinimide in an aprotic, organic solvent such as N,N-dimethylformamide, acetonitrile, ethyl acetate, methylene chloride, or more preferably, tetrahydrofuran in the presence of a carbodiimide such as 1,3-dicyclocarbodiimide, and at a temperature in the range of about 0° to about 40° C. or more preferably 20° C. The resulting ester of formula III may be isolated by conventional means such as crystallization or chromatography, or it may be used directly in the next step of a synthesis of this invention.

Procedure A

An N-oxysuccinimide ester of formula III may be reacted with a uracil polyoxin C compound of formula IV

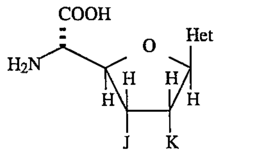

IV wherein J, K, and Het are as described above, to obtain a compound of formula V. The reaction is run in apolar, aprotic, organic solvent such as N,N-dimethylformamide, acetonitrile, tetrahydrofuran, or more preferably, dimethylsulfoxide. The reaction is run under an inert atmosphere such as argon or nitrogen. The reaction is run at a temperature in the range of about to 20° C. to about 50° C., more preferably, at room temperature. The resulting compound of formula V may be separated by conventional means such as crystallization or chromatography, or it may be used directly in the next step of a synthesis of this invention.

Procedure B

A compound of formula V may be reacted with an amine $R_5NR_6$ (wherein $R_5$ and $R_6$ are as described herein) to obtain a compound of formula VI. The reaction is run in a polar, aprotic, organic solvent such as acetonitrile, tetrahydrofuran, or more preferably, dimethylformamide, in the presence of a carbodiimide, such as dicyclohexylcarbodiimide, and in the further presence of an activating reagent such as N-hydroxysuccinimide, or more preferably 1-hydroxybenztriazole. The reaction is run at a temperature in the range of about 0° to about 50° C., more preferably, room temperature. The resulting compound of formula VI may be separated by conventional means such as crystallization or chromatography, or it may be used directly in the next step of the synthesis of this invention.

Amines of the formula $R_5NR_6$ are known, or may be prepared in accordance with known methods.

The next step of the synthesis is the deprotection of the $—NHR_{10}$ group of a compound of formula VI to obtain a compound of formula I.

in the case of the tert-butoxycarbonyl (BOC) protecting group, a compound of formula VI may be converted to a final product of formula I of the invention by treatment with a mineral acid such as hydrochloric acid or sulfuric acid, or more preferably, the organic acid trifluoroacetic acid at a temperature in the range of about 0° C. to about 25° C., more preferably room temperature. A compound of formula I of the invention may be separated from reaction mixture by conventional means such as crystallization or chromatography.

In the case of the benzyloxycarbonyl (CBZ) protecting group, a compound of formula VI may be hydrogenolized by dissolving it in a solvent such as ethanol, or more preferably, 95% methanol and 5% formic acid in the presence of a catalyst which facilitates hydrogenolysis such as palladium on carbon, or more preferably palladium black. After deprotection is complete, the palladium may be filtered and the filtrate evaporated under reduced pressure at 50° C. to obtain a compound of formula I of the invention. This compound of formula I may be further purified by conventional means such as crystallization or chromatography.

Compounds of formulas II and III are known, and may be prepared in accordance with known methods, or else they may be prepared as described herein.

FORMULA SCHEME 2

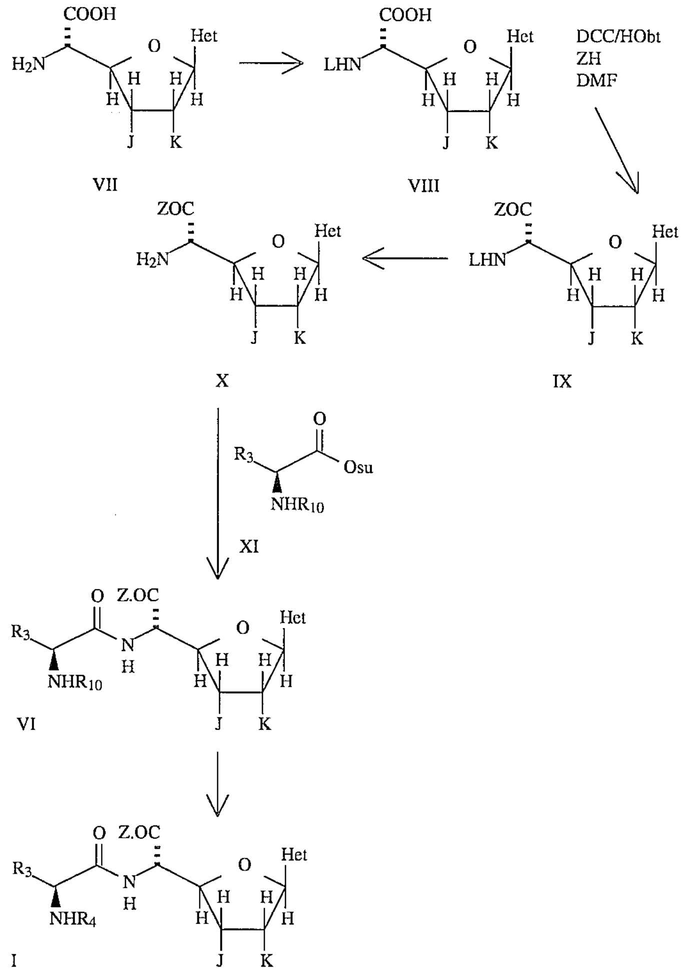

wherein. L is a protecting group or a leaving group such as CBZ or BOC.

Procedure C

A compound of formula VII may be reacted with a protecting group or a leaving group such as benzyloxycarbonyl (CBZ) or, more preferably, BOC (di-tert. butyldicarbonate) to obtain a compound of formula VIII. The solvent employed is a polar solvent such as methanol, N,N-dimethylformamide, or more preferably, water. The reaction is run at a pH in the range of about 8 to about 10, more preferably, 9.5. The reaction mixture is kept basic through use of an alkali metal carbonate such as sodium carbonate or potassium carbonate, or through use of an alkali metal hydroxide such as potassium hydroxide or, more preferably, sodium hydroxide. The reaction is run at a temperature in the range of about 0° to about 25° C., more preferably about room temperature.

The resulting compound of formula VIII may be separated by conventional means such as crystallization or chromatography, or it may be used directly in the next step of the synthesis of this invention.

A compound of formula VIII may be reacted with an amine $R_5NR_6$ as described above, to obtain a compound of formula IX. The reaction is run in a polar, organic solvent such as acetonitrile, tetrahydrofuran, or more preferably, dimethylformamide, in the presence of a carbodiimide, such as dicyclohexylcarbodiimide, and in the further presence of an activating reagent such as N-hydroxysuccinimide, or more preferably 1-hydroxybenztriazole. The reaction is run at a temperature in the range of about 0° to about 50° C., more preferably, room temperature. The resulting compound of formula IX may be separated by conventional means such as crystallization or chromatography, or it may be used directly in the next step of the synthesis of this invention.

Procedure D

A compound of formula IX may be converted to a compound of formula X by reaction in a mineral acid such as hydrochloric acid or sulfuric acid, or more preferably, the organic acid trifluoroacetic acid. The reaction is run at a temperature in the range of about 0° to about 25° C., more preferably room temperature. The resulting compound of formula X may be separated by conventional means such as crystallization or chromatography, or it may be used directly in the next step of the synthesis of this invention.

A compound of formula X may be convened to a compound of formula VI by reaction with a N-oxysuccinimide ester of a N-blocked-amino acid of the formula

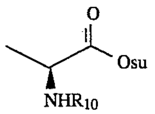

XI wherein $R_{10}$ is as described herein. The reaction is run in an anhydrous polar organic solvent such as methyl sulfoxide, tetrahydrofuran, acetonitrile, or more preferably dimethylformamide, in the presence of a tertiary amine base such as diisopropylethylamine, N-methyl morpholine, or more preferably triethylamine at a temperature in the range of about 0° to about 50° C., or more preferably room temperature. The resulting compound of formula VI may be separated by conventional means such as crystallization or chromatography, or it may be used directly in the next step of the synthesis of this invention.

The next step of the synthesis is the deprotection of the —$NHR_{10}$ group of a compound of formula VI to obtain a compound of formula I.

In the case of the tert-butoxycarbonyl (BOC) protecting group, the compound of formula VI may be converted to a final product of formula I of the invention by treatment with a mineral acid such as hydrochloric acid or sulfuric acid, or more preferably, the organic acid trifluoroacetic acid, at a temperature in the range of about 0° to about 25° C., more preferably room temperature. The compound formula I of the invention may be separated from the reaction mixture by conventional means such as crystallization or chromatography.

In the case of the benzyloxycarbonyl (CBZ) protecting group, a compound of formula VI may be hydrogenolized by dissolving it in a ethanol, or more preferably, 95% methanol and 5% formic acid in the presence of a catalyst which facilitates hydrogenolisis such as palladium on carbon, or more preferably, palladium black. After deprotection is complete the palladium may be filtered and the filtrate evaporated under reduced pressure at 50° C. to obtain a compound of formula I of the invention. This compound of formula I may be further purified by conventional means such as crystallization or chromatography.

Compounds of formulas VII and XI are known, may be prepared in accordance with known methods, or else they may be prepared as described herein.

The compounds of formula I of the invention are useful as agents for treating fungi. Compounds of formula I of the invention were tested and found to be active as anti-fungal agents using procedures set forth below.

RESULTS

The minimum inhibitory concentrations (MIC-R and MIC-S) for a series of compounds of formula I of the invention are as shown in Table 1 below. Mass spectrum (MS) molecular ion masses are also shown in this table.

The test results shown below (MIC-R and MIC-S) were obtained from the test procedures set forth just below.

In vitro anti-fungal activity was determined in microtiter minimum inhibitory concentration (MIC) tests using Yeast Nitrogen Broth (YNB without amino acids, Difco., Detroit, Michigan) at pH 5.4. Yeasts were grown overnight in Sabouraud Dextrose Broth at 28° C. with shaking, and concentrations adjusted in sterile saline using a spectrophoptometer at 540 mµ. Compounds were dissolved in various vehicles and diluted in media to twice the final concentrations. The Cetus Pro/Pette system was used to serially dilute 50 µl in round bottom 96 well plates (Falcon, Lincoln Park, N.J.). The turbidometrically adjusted yeast suspensions were diluted 1:3,000 in YNB. These dilutions when added to the wells, produced a final inoculum of $3\times10^3$/ml. Plates were incubated at 37° C. for 48 hours. MICs were defined as the lowest concentrations of compound that prevented visible growth. MICs were taken against the following organisms and expressed in the table above as the geometric mean.

MIC-R and MIC-S mean respectively MICs taken against resistant and sensitive strains.

Resistant Strains

*Candida albicans* C79
*Candida albicans* C6
*Candida albicans* C8
*Candida albicans* C31
*Candida albicans* C54
*Candida albicans* C70
*Candida albicans* C104
*Candida albicans* C138
*Candida albicans* C140
*Candida stellatoidea* C45

Sensitive Strains

*Candida albicans* C141
Candida sp. C2
Candida sp. C109
*Candida parapsilosis* C67
*Candida tropicalis* C112
*Torulopsis glabrata* C95
*Candida pseudotropicalis* C 967
*Candida guillermondii* C137
Sacchararomyces C78
Sacchararomyces mutant C147

TABLE 1
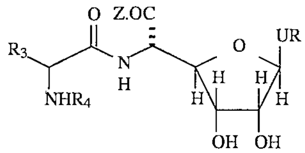
| No. | 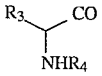 | Z.OC | MIC-R μg/ml | MIC-S μg/ml | MS |
|---|---|---|---|---|---|
| 1. | 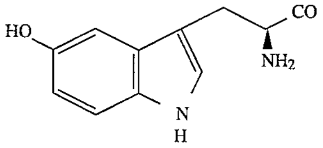 | $CONH(CH_2)_3CH_3$ | >4096 | >4096 | 544 |
| 2. | 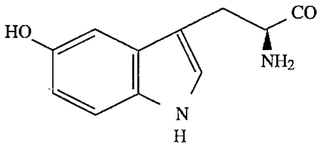 | $CONH(CH_2)_7CH_3$ | 478 | 460 | 600 |
| 3. | 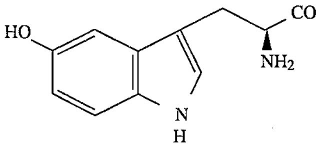 | $CONH(CH_2)_{11}CH_3$ | 23 | 478 | 657 |
| 4. | 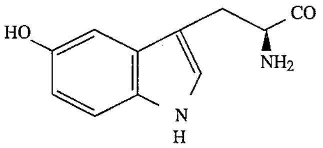 | $CONH(CH_2)_{17}CH_3$ | >2048 | >2048 | 740 |
| 5. | 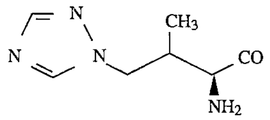 | $CONH(CH_2)_{11}CH_3$ isomer 1 | >256 | >256 | 620 |
| 6. | 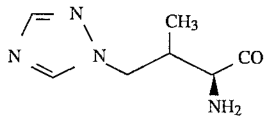 | $CONH(CH_2)_{11}CH_3$ isomer 2 | 74 | 181 | 620 |
| 7. | 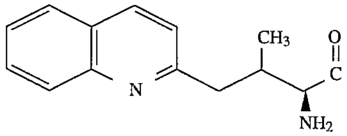 | $CONH(CH_2)_{11}CH_3$ isomer 1 | 17 | 103 | 680 |
| 8. | 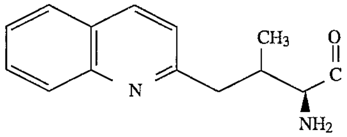 | $CONH(CH_2)_{11}CH_3$ isomer 2 | >256 | 158 | 680 |
| 9. | 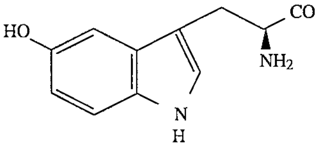 | $CONH(CH_2)_{13}CH_3$ | >256 | 147 | 684 |

TABLE 1-continued
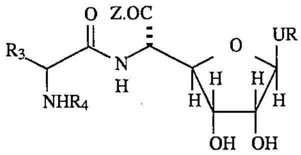
| No. | 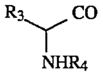 | Z.OC | MIC-R μg/ml | MIC-S μg/ml | MS |
|---|---|---|---|---|---|
| 10. | 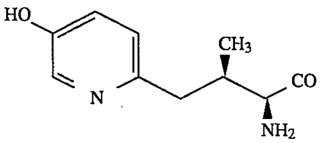 | $CONH(CH_2)_{11}CH_3$ | 147 | 478 | 646 |
| 11. | 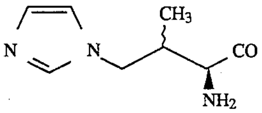 | $CONH(CH_2)_{11}CH_3$ | 316 | 85 | 659 |
| 12. | 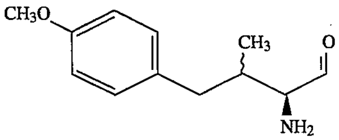 | $CONH(CH_2)_{11}CH_3$ | 28 | 208 | 659 |
| 13. | 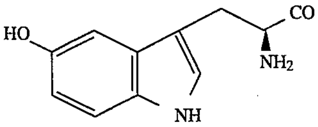 | $CONH(CH_2)_9CH_3$ | 181 | 388 | 628 |
| 14. | 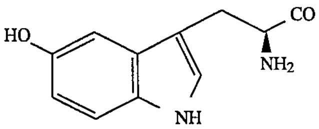 | $CON(OBZL)(CH_2)_{11}CH_3$ | 28 | 119 | 762 |
| 15. | 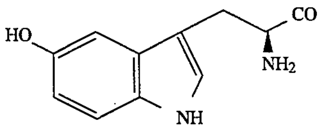 | 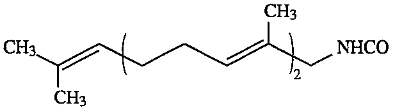 | 143 | 362 | 692 |
| 16. | 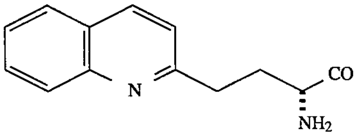 | $CONH(CH_2)_{11}CH_3$ | 294 | 239 | 666 |
| 17. | 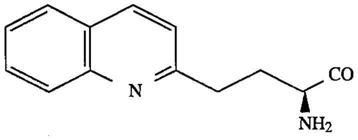 | $CONH(CH_2)_{11}CH_3$ | 21 | 158 | 666 |
| 18. | 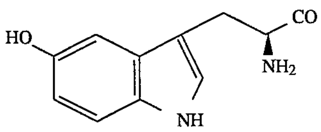 | $CON(OH)(CH_2)_{11}CH_3$ | 39 | 239 | 672 |
| 19. | 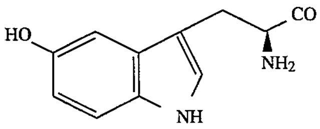 | 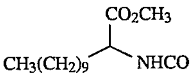 | 111 | 194 | 700 |

TABLE 1-continued

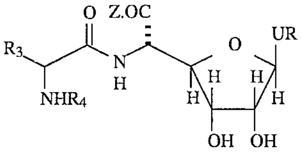

| No. | 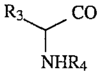 | Z.OC | MIC-R μg/ml | MIC-S μg/ml | MS |
|---|---|---|---|---|---|
| 20. | 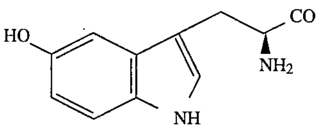 | 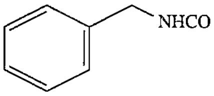 | >256 | >256 | 578 |
| 21. | 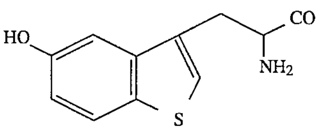 | $CONH(CH_2)_{11}CH_3$ isomer 1 | 208 | 158 | 673 |
| 22. | 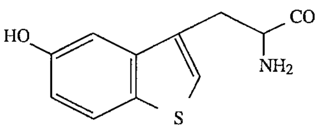 | $CONH(CH_2)_{11}CH_3$ isomer 2 | >256 | 158 | 673 |
| 23. | 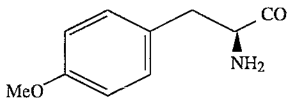 | $CONH(CH_2)_{11}CH_3$ | 9.8 | 56 | 631 |
| 24. | 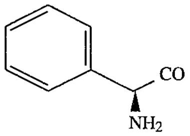 | $CONH(CH_2)_{11}CH_3$ | 18 | 194 | 587 |
| 25. | 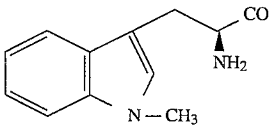 | $CONH(CH_2)_{11}CH_3$ | >256 | >256 | 654 |

As can be seen from the above table, compounds of the invention exhibit anti-fungal activity against human and animal pathogens which are both sensitive to nikkomycins (MIC-S μg/ml<128) and resistant to nikkomycins (MIC-R μg/ml>2048).

In vivo anti-fungal activity was tested for in the following test protocol. Compounds of the invention were found to be active in the following test protocol.

MATERIALS & METHODS

Vaginal Candida Infections in Hamsters

*C. albicans* (C60 or C79), clinical isolates, were grown on SDA slants for 48 h at 28° C. Cells were washed off the slants with SDB broth to obtain a suspension of approximately $1\times10^8$ cells/ml. Groups of 10 female Syrian outbred hamsters (Charles River), weighing 100–120 grams, were used. On the first day of the experiment, the vagina was swabbed with a dry cotton swab to remove any mucus and to induce a slight irritation. The suspension of *C. albicans* (0.05 ml) was introduced into the vagina on three successive days using a syringe equipped with a blunt needle. Two days after infection, samples were obtained for culture by inserting a sterile cotton swab into the vagina. The swabs were placed into 10 ml of 0.9% saline containing cycloheximide (Actidione, Upjohn, 0.45 g/l) and chloramphenicol (Chloromycetin sodium succinate, Parke Davis, Morris Plains, N.J., 0.1 g/l), and then vigorously agitated to dislodge the vaginal sample. A 2 ml aliquot of each sample was then passed through a 0.45 micron Millipore filter. Following a saline rinse of the filters, the filters were placed onto mycosel agar plates and incubated at 37° C. After 48 h the number of *C. albicans* colonies on the filters were counted. Only animals that showed positive cultures were used for the experiments.

Treatment began 4 days after completion of infection. Compounds were solubilized in ethanol:PEG400: glycerol (10:45:45). Treatment was intravaginally at concentrations of 0.125–2% once daily for 4 days. Using cotton swabs, vaginal samples were obtained after 2, 4, 7 and 9 days of treatment and the swabs were processed as above. Efficacy was determined on the basis of negative cultures at each of the four time periods.

MATERIALS & METHODS

*C. albicans* Infection Studies in Mice ($PD_{50}$)

*C. albicans* Wisconsin (C 43) and *C. tropicalis* (C 112), grown on Sabouraud dextrose agar (SDA) slants for 48 h at 28° C., were suspended in saline and adjusted to 46% transmission at 550 nm on a spectrophotometer. The inoculum was further adjusted by hemacytometer and confirmed by plate counts to be approximately 1 or $5\times10^7$ CFU/ml. CF-1 mice (white, male, ca. 20 g, Harlan Sprague Dawley, inc., Indianapolis, Ind.) were infected by injection 1 or $5\times10^6$ CFU into the tail vein. Antifungal agents were administered intravenously or subcutaneously in ethanol: water (10:90), 4 h post infection and once daily thereafter for 3 or 4 more days. Survival was monitored daily. The protective dose50 ($PD_{50}$) was defined as that dose which allowed for 50% survival of mice.

The pharmaceutical compositions of the present invention may be formulated by combining a compound of the invention or pharmaceutically acceptable salt thereof with any suitable diluent, i.e., inert pharmaceutical carrier or diluent adapted for administration orally, parenterally, topically, vaginally or rectally.

Examples of suitable compositions include solid or liquid compositions for oral administration such as tablets, capsules, pills powders, granules, solutions, suspensions or emulsions. They may also be manufactured in the form of sterile solid compositions which can be dissolved in sterile water, physiological saline or some sterile injectable medium immediately before use.

Topical dosage forms may be prepared according to procedures well known in the art, and may contain a variety of ingredients, excipients, and additives. The formulations for topical use include ointments, creams, lotions, powders, aerosols, pessaries, and sprays. Of these, lotions, ointments, and creams, may contain water, oils fats, waxes, polyesters, alcohols or polyols, plus such other ingredients as fragrances, emulsifiers, and preservatives. Powders are made by mixing the active ingredient with a readily available, inert, pulverous distributing agent such as talcum, calcium carbonate, tricalcium phosphate, or boric acid. Aqueous suspensions of the above powders may also be made. Solutions or emulsions may also be prepared using inert solvents which are preferably nonflammable, odorless, colorless, and nontoxic, for example, vegetable oils, isopropanol, dimethyl sulfoxide, hydrogenated naphthalenes, and alkylated naphthalenes. Similarly, aerosol, and non aerosol sprays may be prepared using solutions or suspensions in appropriate solvents, for example, difluorodichloromethane for aerosols.

Parenteral forms to be injected intravenously, intramuscularly, or subcutaneously, are usually in the form of a sterile solution, and may contain salts or glucose to make the solution isotonic.

Compounds of the invention may also be incorporated in vaginal or rectal suppositories. Suppositories may be prepared by methods which are conventional in the art. In addition to comprising a compound of the invention, suppositories may contain a suppository base made up of biocompatible polymers, a surfactant, and an absorbent in a vegetable oil phase.

In addition, the suppositories may be further modified by inclusion of an antioxidant.

When used orally or parenterally, the compounds of the invention can be administered in an amount ranging from about 0.02 mg/kg body weight to about 40.0 mg/kg body weight, preferably from about 0.1 mg/kg body weight to about 20 mg/kg body weight per day.

Determination of the proper dosage of a compound of the invention for a particular situation is within the skill of the art. Generally, treatment is initiated with smaller dosages that are less than the optimum dose of the compound, Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition, size of the patient, severity of the symptom being treated, and the pharmacokinetics of the particular compound being employed.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

Preparation of N-BOC-UPOC

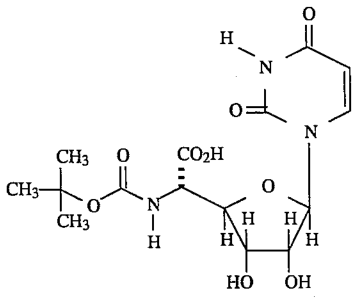

UPOC (8 g, 27.8 mmol) was dissolved in 200 ml of distilled water. The solution was stirred and the pH was adjusted to 9.5 with 20% sodium hydroxide solution. At room temperature di-tert. butyldicarbonate (8 g, 36.7 mmol) was added all at once and stirred while the pH was monitored at 9.5 with sodium hydroxide. After approximately 5 hours or after the reaction was complete by thin layer chromatography (tlc) (40 % methanol-methylene chloride, normal phase silica plates) Dowex XFS-43279.00 hydrogen from resin was added to pH 3.0. The resin filtered off and the solvents were evaporated off under reduced pressure at 45° C. The resulting solid was dissolved in 100 mL of methanol and added to stirring ether. The precipitate was filtered off and dried in a vacuum desiccator to obtain 10.5 g (97%) of the title product.

$^1$H-NMR (300MHZ, $CD_3OD$) δ7.70 ( 1H, d, J=7.5Hz), δ5.92 (1 H, d, J=6Hz), δ5,70 (1 H, d, J=7.5Hz), δ4.39 (1 H, m,), δ4.32 (1H, m), δ4.23 (1H, m), δ4.12 (1H, t, J=5.25 Hz), δ1.45 (1H,s).

EXAMPLE 2

Preparation of N-BOC.6'-dodecylamido-UPOC

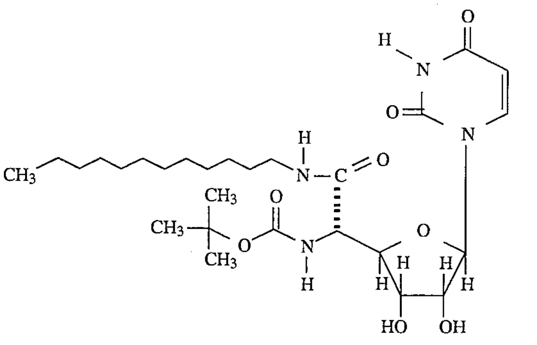

N-BOC-UPOC (5.2 g, 13.42 mmol) was dissolved in 150 ml of dry N,N-dimethylformamide (DMF). Dodecylamine (3.73 g, 20.13 mmol), dicyclohexylcarbodiimide (5.538 g, 26.84 mmol), and 1-hydroxybenztriazole ( 2.26 g, 16.77 mmol)were added and the resulting mixture was stirred at room temperature. After 48 hours 2 ml of $H_2O$ were added and the resulting mixture was stirred for 15 minutes. The precipitate was filtered off and the solvent, DMF, was evaporated under high vacuum at 50° C. to obtain an oil. The oil was chromatographed on silica gel using 1.25% to 5% methanol-methylene chloride to obtain 6.3 g (84%) of the title product.

EXAMPLE 3

6'-Dodecylamido-UPOC-trifluoroacetate

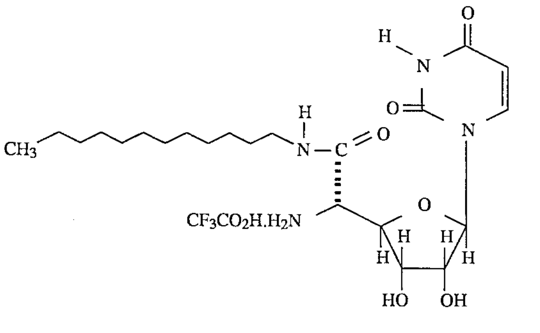

N-BOC-6'-dodecylamido-UPOC (6.25 g, 11.25 mmol) were dissolved in 15 ml of trifluoroacetic acid and the resulting mixture was stirred at room temperature for 5 minutes. 100 ml of ether were added and the solids were filtered off to obtain 6.01 g of title product after drying in a vacuum desiccator.

$^1$H-NMR (300 MHZ, $D_2O$) δ7.62 (1 H, d, J=8.07 Hz), 5.66 (1H, d, J=8.01 Hz), 5.49 (1H, d, J=8.87 Hz) 4.28 to 4.34 (2H, m), 4.16 (1H, t, J=4.95 Hz), 4.08 (1H, d, J=5.22 Hz),1.46 (2H, m), 1.22 (20H, br.s), 0.835 (3H,t, J=6.99 Hz).

EXAMPLE 4

Preparation of 5-N-(α-N-BOC-5-hydroxy-tryptophanyl)-UPOC

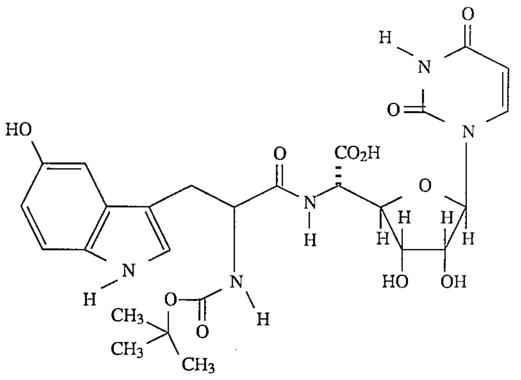

To a mixture of UPOC (3.3 g, 11.4 mmol) in 350 ml of DMSO and 9 ml of NMM were added the N-oxysuccinimide ester of L-5-hydroxytryptophan (7.6 g, 17.5 mmol) and the resulting mixture was stirred at room temperature under a dry nitrogen atmosphere. After 24 hours 600 ml of ether were added and the resulting mixture was stirred for 5 minutes. The mixture was allowed to settle and the supernatent ether-DMSO solution was decanted off. This sequence was repeated two more times to obtain a gummy solid. The gummy solid was chromatographed on C-18 reverse phase silica gel using 10 to 50 % methanol/water gradient to obtain 2.34 g (35 %) of title product. FABMS 590.2 ($M^+$+1).

EXAMPLE 5

Preparation of 6'-Dodecylamido-5-N-(5-hydroxytryptophanyl)UPOC

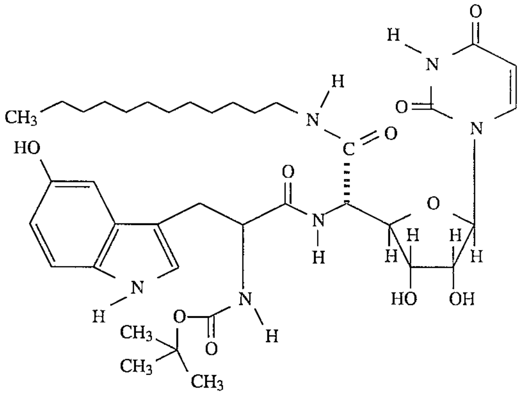

5-N-(L-N-BOC-5-hydroxy-tryptophanyl)-UPOC (0.2 g, 0.4 mmol) were dissolved in 10 ml of DMF. Hydroxybenztriazole (0.081 g, 0.6 mmol) and DCC (0.12 g, 0.6 mmol) and n-dodecylamine (0.11 g, 0.6 mmol) were added and the solution was stirred at room temperature. After 24 hours, 1 ml of water was added and the resulting mixture was evaporated to dryness under vacuum at 50° C. The residue was chromatographed on silica gel using a mixture of 10% methanol/methylene chloride as the eluent to obtain 0.107 g of pure blocked product. The blocked product was dissolved in 1 ml of trifluoroacetic acid and allowed to stand for 5 minutes. Ether was added and the pure title product 0.1 g (35 %) was filtered off.

FABMS 657 ($M^+$+1), ACC. MASS for $C_{33}H_{49}N_6O_8$ 657.3612 found 657.3613.

EXAMPLE 6

Preparation of 2-N-fluorenylphenyl-3-methyl-4-(p-methoxyphenyl)-4-hydroxy-butyryllactone

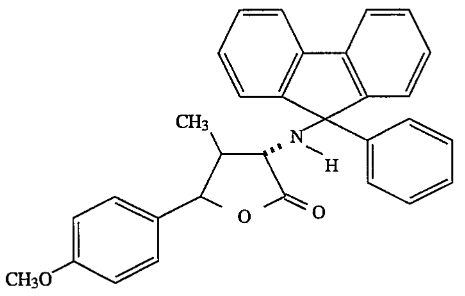

3-S-N-fluorenylphenyl-2-methyl-3-carboxymethyl-butyral [(see H. Rapaport and J. Wolf, J. Org. Chem. 1989, 54, 3164–3173 (1.38 g, 3.57 mmol)] was dissolved in 5 ml of tetrahydrofuran (THF). The solution was cooled to 0° under a dry nitrogen atmosphere. 7.14 mmol of 4-anisole Grignard reagent was added and the mixture was stirred for 4 hours. The reaction mixture was added to 50 ml of saturated ammonium chloride solution and the product was extracted with three 50 ml portions of ethyl acetate. The ethyl acetate extracts were dried over magnesium sulfate, filtered, and evaporated to an oil. The oil was chromatographed on a silica gel column using a mixture of 5% ethyl acetate/hexane as the eluent to obtain 0.58 g (36%) of title product in a 3/1 mixture of trans/cis isomers.

$^1$H-NMR (300 MHZ, CDCL$_3$) δ6.6 to 7.8 (18H, m), 5.47 (d, J=7.23 Hz) and 4.91 (d, J=7.2 Hz) total of 1H in a ratio of 3/1 respectively, 3.75 and 2.86 (1H, two d, J=7.02 in a ratio of 3/1 respectively, 3.73 and 3.76 (3H two s in a ratio of 3/1 respectively), 2.25 and 2.55 (1H, m), 0.66 and –0.08 (1H, two d, J=7.11 in a ratio of 3/1 respectively.

EXAMPLE 7

Preparation of 2-S-N-BOC-amino-3-R,S-methyl-4-P-methoxyphenyl-butyric acid

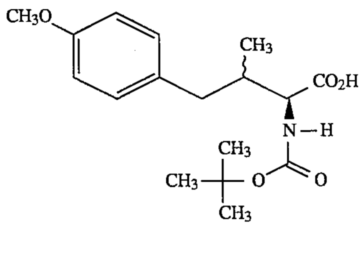

To 2-N-fluorenylphenyl-3-R,S-methyl-4-(p-methoxyphenyl)- 4-hydroxy-butyryllactone (0.48 g) were added 100 ml of methanol and 50 ml of 1N HCl and the starting material was hydrogenated over a catalytic amount of 5% palladium on charcoal for 4 hours. The palladium on charcoal filtered off and the pH was adjusted to 9.5 with 1N sodium hydroxide solution. 0.3 g of di-tert.-butyl-dicarbonate was added and the resulting mixture was stirred for one hour. The reaction mixture was added to an excess of 5% citric acid and the product was extracted with three 50 ml portions of methylene chloride. The methylene chloride layers were tided over magnesium sulfate, filtered, and evaporated to obtain an oil. The oil was chromatographed on a silica gel column using a mixture of 5% methanol/methylene chloride to obtain 0.16 g (68%) of the title product.

$^1$H-NMR (300 MHZ, CDCL$_3$) δ7.10 ( 2H, d, J=8.49 Hz), 6.82 and 6.84 (2H, two d, J=8.49 Hz), 5.07 and 5.16 (1H, two d, J=8.55 and 9.48 Hz respectively), 4.40 (1H, m), 2.74 (1H, m), 2.31 (2H, m) 1.46 (9H, s), 0.86 (3H, m).

EXAMPLE 8

Preparation of 5-N-(2-S-N-BOC-amino-3-R,S-methyl-4-p-methoxyphenylbutyryl)-UPOC

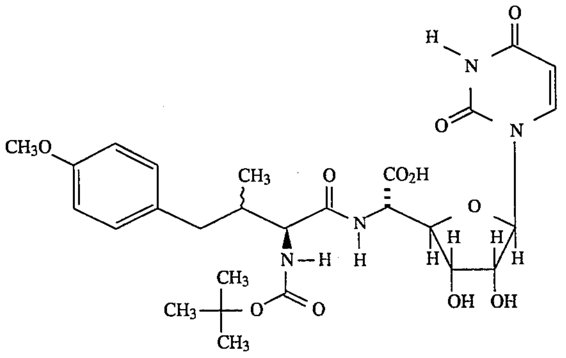

To a mixture of UPOC (0.287 g, 1 mmol) in 40 ml of DMSO and 0.8 ml of NMM were added the N-oxysuccinimide ester of 2-S-N-BOC-amino- 3-methyl-4-p-methoxyphenyl-butyric acid ( 0.88 mmol) and the resulting mixture was stirred at room temperature under a dry nitrogen atmosphere. After 24 hours, 60 ml of ether were added and the mixture was stirred for 5 minutes. The mixture was allowed to settle and the supernatent ether-DMSO solution was decanted off. This sequence was repeated two more times to obtain a gummy solid. The gummy solid was chromatographed on C-18 reverse phase silica gel 10 to 50 % methanol/water gradient to obtain 0.099 g (16%) of title product.

MS m/e (493.4, $M^+$+1).

EXAMPLE 9

Preparation of 6'-Dodecylamido-5-N-(2-S-amino-3-R,S-methyl-4-p-methoxyphenyl-butyryl) UPOC

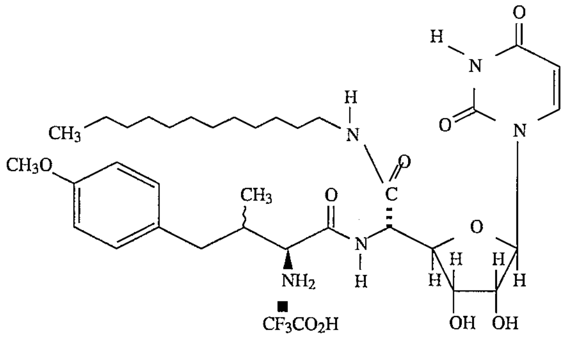

5-N-(2-S-N-BOC-amino-3-R,S-methyl4-p-methoxyphenylbutyryl)-UPOC (0.099 g, 0.16 mmol) were dissolved in 5 ml of dimethylformamide (DMF). Hydroxybenztriazole (0.032 g, 0.24 mmol) and DCC (0.05 g, 0.24 mmol) and n-dodecylamine (0.045 g, 0.24 mmol) were added and the solution was stirred at room temperature. After 24 hours, 0.5 ml of water was added and the mixture was evaporated to dryness under vacuum at 50° C. The resulting mixture was chromatographed on silica gel using a mixture of 10% methanol/methylene chloride as the eluent to obtain 0.06 g of pure blocked product. The blocked product was dissolved in 1 ml of trifluoroacetic acid and allowed to stand for 5 minutes. Ether was added and pure title product 0.051 g ( 42 %) was collected by filtration.

ACC. MASS for $C_{34}H_{54}N_5O_8$ 660.3972, found 660.3930.

EXAMPLE 10

Preparation of 1-chloro-2-(4-methoxypheny)-ethane

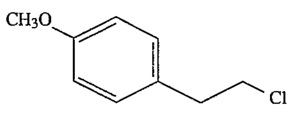

4-methoxy-phenethyl alcohol (15.2 g, 10 mmol) were dissolved in 200 ml of dichloromethane and at 0° C., 7.35 ml of thionyl chloride were added. The reaction mixture was allowed to warm to room temperature over ½ hour. After stirring for 20 hours, the mixture was added to brine and extracted with dichloromethane. The dichloromethane was evaporated to obtain an oil which was chromatographed on silica gel using a mixture of 30% ethyl acetate/hexane as the eluent to obtain 8.8 g (51%) of the title product.

$^1$H-NMR (300 MHz, $CDCl_3$) δ7.17 (2H, d, J=8.5 Hz), 6.88 (2H, d, J=8.5 Hz), 3.81 (3H,s), 3.69 (2H, t, J=7.68 Hz), 3.03 (2H, t, J=7.68 Hz).

EXAMPLE 11

Preparation of 2-L-S-N-BOC-amino-4-p-methoxyphenylbutyric acid

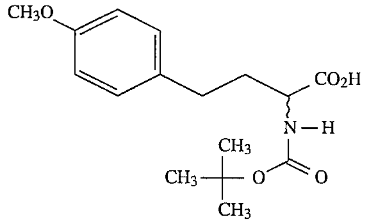

Diethylformamidomalonate (15.2 g, 75 mmol) were dissolved in 100 ml of DMF and the resulting mixture was cooled under a nitrogen atmosphere in an ice bath. A 60% oil dispersion of sodium hydride (3 gm) was added portionwise and the resulting mixture was stirred for one hour. 1-Chloro-2-(4-methoxypheny)-ethane (8.8 gm, 52 mmol) were dissolved in DMF and added to a stirring sodium diethylformamidomalonate mixture and heated to 80° C. After 4 hours the resulting mixture was added to brine and extracted with dichloromethane. The dichloromethane extracts were dried over magnesium sulfate and filtered. The solvent was evaporated under reduced pressure. The product was chromatographed on silica gel using a mixture of 50% ethyl acetate/hexane to obtain 11.01 g of product. 250 ml of 10% HCl were added and the mixture was refluxed for 2 hours. The water and HCl were evaporated off. To the resulting solid was added 100 ml of water and 25 ml of methanol. The pH was adjusted to 10.0 with 25% sodium hydroxide and 10 g of di-tert. butyldicarbonate were added The mixture was stirred for 1 hour. The mixture was added to 500 ml of 5% citric acid and the resulting mixture was extracted with 3×200 ml portions of dichloromethane. The extracts were dried over magnesium sulfate, and filtered. The solvent was evaporated off under reduced pressure. The resulting solid was chromatographed on silica gel using a mixture of 5% methanol/dichloromethane to obtain 6.71 g (43%) of the title product.

$^1$H-NMR (300 MHz, $CDCl_3$) δ7.12 (2H, d, J=8.55 Hz), 6.83 (2H, d, J=8.55 Hz), 5.04 (1H, d, J=7.8 Hz) 4.35 (1H, m), 3.79 (3H, s), 2.67 (2H, t, J=7.92 Hz), 1.92–2.19 (2H, m), 1.46 (9H, s).

EXAMPLE 12

Preparation of 3-[(diethoxyphosphino)oxy]-2-methoxyimino-3-methylpropanoate

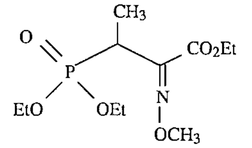

To a solution of ethyl 3-[(diethoxyphosphino)oxy]-2-methoxyiminopropanoate (30g, 0.11 mole *Tetrahedron Lett.*, 1988, 29 3361) in dimethylsulfoxide (DMSO) (150 ml) at 5°–8° C. was added potassium t-butoxide (13.7 g, 0.12 mole) in small portions. The mixture was heated at 60° C. for 2 hours, then cooled to 5°–8° C. and methyl iodide (7.3ml, 0.12 mole) was added. The mixture was heated at 40° C. for 6 hours, poured into an ice-cold solution of ammonium chloride (1000 ml), and extracted with methyl isobutyl ether. The ethereal extracts were evaporated and the residue was chromatographed (silica gel, 3:7 EtoAc—hexane) to obtain 17 g (54%) of the title compound.

$^1$H-NMR (200 MHz, $CDCl_3$) δ3.8 to 4.15 (7H, complex m), 4.02 (3H, s), 1.20 to 1.60 (9H, complex m).

EXAMPLE 13

Preparation of Ethyl-2-methoxyimino-3-methyl-4-(2-quinolino)- 3-butenoate

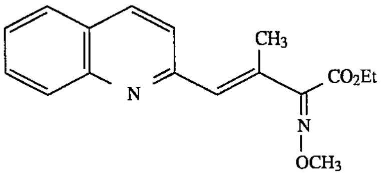

Ethyl-2-methoximino-3-methyl-3-ethylphosphonatepropionate (3.6 g, 12.2 mmol) were dissolved in 57 ml of DMF at room temperature under a dry nitrogen atmosphere. A 60% oil dispersion of sodium hydride (0.58 g, 14.6 mmol) was added portionwise and the resulting mixture was stirred for 1 hour. Solid 2-quinolinecarboxaldehyde (1.59 g, 12 mmol) was added. After stirring for 4 hours, the reaction mixture was added to 5% citric acid and the resulting mixture was extracted with 3×100 ml of dichloromethane. The dichloromethane evaporated off and the resulting mixture was chromatographed on silica gel using a mixture of 10% ethylacetate/hexane to obtain 1.8 g (50%) of the title product.

FABMS 299.0 ($M^+$+1).

EXAMPLE 14

Preparation of 2-R,S-N-BOC-amino-3-R,S-methyl-4-(2-quinolinyl)butyric acid

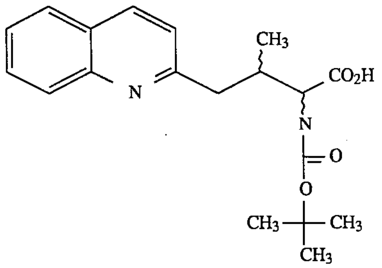

Ethyl-2-methoxyimino-3-R,S-methyl-4-(2-quinolino)-3-butenoate (1.8 g, 6 mmol) was dissolved in 37 ml of methanol. 37 ml of 1N potassium hydroxide were added and the resulting mixture stirred at room temperature. After hydrolysis of the ethyl ester was complete, at approximately 3 hours, as evidenced by thin layer chromatography (tlc) (20% methanol/dichloromethane) 12.4 g of nickel/aluminum amalgam were added and the resulting mixture was stirred. The temperature was allowed to rise to about 50° C. After stirring about four hours, the reaction mixture was filtered on a celite pad and the pH of the filtrate was adjusted to 11 with 6N hydrochloric acid. The white precipitate was filtered off. 1.6 g of di-tert.-butyldicarbonate were added and the reaction mixture was stirred with the pH being adjusted to 9.5 as necessary. After 1 hour the reaction was complete. The reaction mixture was added to 400 ml of 5% citric acid and extracted with 3×150 ml of dichloromethane. The dichloromethane was evaporated off and chromatographed. The resulting oil was chromatographed on silica gel using a mixture of 5% methanol/dichloromethane to obtain 1.68 g (81%) of the title product as an 8/2 mixture of diastereomers.

$^1$H-NMR (300 MHz, $CDCl_3$) of the first diastereomer: δ8.34 (1H, d, J=8.52 Hz), 8.06 (1H, d, J=8.55 Hz), 7.90 (1H, d, J=7.95 Hz), 7.81 (1H, t, J=8.32 Hz), 7.64, t, J=7.86 Hz), 7.49 (1H, t, J=8.4 Hz), 5.723 (1H, d, 7.92 Hz), 4.30 (1H, dd, J=4.62 and 6.78 Hz), 3.163 (2H, m), 2.52 (1H,m), 1.45 (9H, s), 1.14 (3H, d, J=6.78 Hz); second diastereomer 8.29 (1H, d, J=8.34 Hz), 8.19 (1H, d, J=8.52 Hz), 7.88 (1H, d, J=7.92 Hz), 7.80 (1H, t, J=7.11 Hz), 7.62 (1H, t, J=7.35 Hz), 7.41 (1H, d, J=8.40), 5.57 (1H, d, J=7.92 Hz), 4.31 (1H, t, J=7.95 Hz), 3.29 (2H, m), 2.49 (1H, m), 1.42 (9H, s). 1.05 (3H, d, J=7.05 Hz). FABMS 345.0 ($M^+$+1).

EXAMPLE 15

Preparation of Methyl-2-S-N-fluorenylphenylamino-3-R,S-methyl-4-bromo butyrate

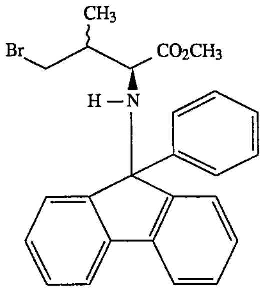

1 g of methyl-2-S-N-fluorenylphenyl-3-R,S-methyl-4-hydroxy butyrate (preparation as described in H. Rapoport and J. Wolf, J. Org. Chem. 54, 3164 (1989)) was dissolved in tetrahydrofuran. Carbon tetrabromide (1.57 g) and triphenylphosphine (1.26 g) was added and the mixture was stirred at room temperature for 4 hours. The mixture was added to brine and extracted with ethyl acetate. The ethyl acetate layer was dried over magnesium sulfate, filtered, and evaporated to dryness. The mixture was chromatographed on a silica gel column using a mixture of 5% ethyl acetate/hexanes as the eluent to obtain 1.07 g of the title product.

$^1$H-NMR (300 MHZ, $CD_3OD$) δ1.06 (3H, d, J=6.8 Hz), 1.84–1.90 (1H, m), 3.21 (2H, d, J=6.8 Hz), 3.28 (3H, s), 7.162–7.47 (13H,m). FABMS 450 ($M^+$+1).

EXAMPLE 16

Preparation of 2-S-N-fluorenylphenylamino-3-R,S-methyl-4-([1]H-1,2,4-triazolyl)butyric acid

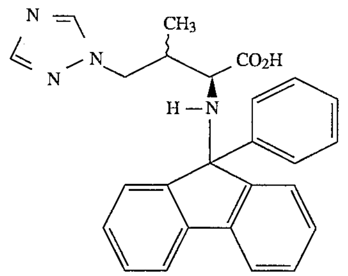

Methyl-2-S-N-fluorenylphenyl-3-R,S-methyl-4-bromobutyrate (1.34 g, 3mmol) were dissolved in 10 ml of N,N-dimethylformamide. Sodium-1,2,4-triazole (0.32 g, 3.5 mmol) was added and the mixture was stirred at room temperature. After 18 hours the mixture was added to brine and the product was extracted with methylene chloride. The methylene chloride layer was dried with magnesium sulfate, filtered, and evaporated to dryness. The resulting mixture was chromatographed on a silica gel column eluting with 30% ethyl acetate/hexane to obtain 0.85 g of the title product as the methyl ester. The methyl ester was dissolved in distilled water/dioxane (10 ml/ 20 ml) and 1 g of potassium hydroxide was added. The mixture was heated to 80° C. for 45 minutes and acidified with citric acid. The product was extracted into methylene chloride to obtain the title product, 0.82 g.

$^1$H-NMR (300 MHZ, $CD_3OD$) δ0.86 & 0.89 (3H, two sets of doublets, J=6.9 Hz), 2.1–2.3 (1H, m), 3.83–3.97(2H, m), 4.3(1H, dd, J=13.98 & 8.34 Hz), 7.16–7.43(13H, m).

EXAMPLE 17

Preparation of 2-S-N-fluorenylphenylamino-3-R,S-methyl- 4-(1-imidazolyl)butyric acid

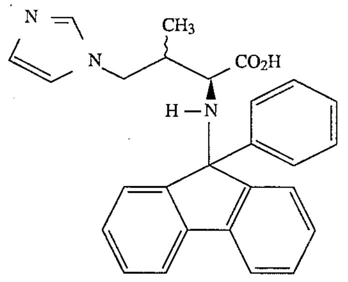

The preparation of this compound was identical to the preparation of 2-S-N-fluorenylphenyl-3-R,S-methyl-4-($^1$H-1,2,4-triazolyl)butyric acid except sodium imidazole was used instead of sodium triazole.

EXAMPLE 18

Preparation of 2-[(benzyloxycarbonyl)amino]-4-(5-hydroxy-2-pyridyl)-3-R,S-methylbutanoic acid

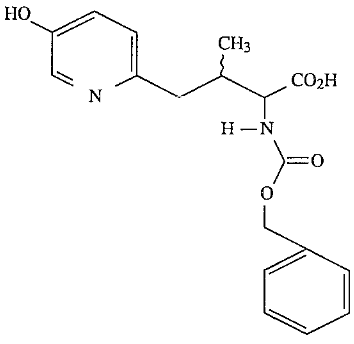

A. Methoxyethoxymethyl chloride (MEM) (19 g, 153 mmol) was added to a solution of 5-hydroxy-2-pyridinecarboxaldehyde (18.4 g, 149 mmol) in 300 ml DMF. NaH (6.3 g of 60% oil dispersion, 158 mmol) were added in portions while cooling the mixture to maintain 20°–30° C. The mixture was stirred an additional 1 hour at 25° C. 5 ml water were added, most of the solvent was evaporated, and water was added to the residue,The mixture was extracted with EtOAc. The extracts were dried over $Na_2SO_4$, filtered, and evaporated to a residue. The residue was chromatographed on silica gel eluting with EtOAc-hexanes (35:65) to obtain 5-[(2-methoxyethoxy)methoxy]-2 -pyridinecarboxaldehyde: $C_{10}H_{13}NO_4$ (211.22); $^1$H-NMR ($CDCl_3$) δ 10.01 (s,1), 8.52 (d,1), 7.93 (d,1), 7.49 (m,1), 5.39 (s,2), 3.80 (m,2), 3.53 (m,2), 3.32 (s,3).

B. NaH (3.9 g of 60% oil dispersion, 98 mmol) was added in portions to a solution of triethylphosphonopropionate (22 g, 92 mmol) in 200 ml THF. The mixture was then added slowly to a stirring a solution of 5-[(2-methoxyethoxy)methoxy]-2 -pyridinecarboxaldehyde (18.5 g, 88 mmol) in 50 ml THF at 15°–25° C., and the resulting mixture was stirred 18 hours at room temperature. The THF supernatant liquid was decanted, the residue was dissolved in water, and 2N HCl was added to adjust the pH to 4.0. The mixture was extracted with hexane. The extracts were combined, the THF supernatant was decanted and evaporated. The residue was extracted with hexanes. The extracts were dried over $Na_2SO_4$, filtered, and evaporated to leave ethyl 3-[5-[(2methoxyethoxy)methoxy] -2-pyridyl]-2-methylpropenoate (23.9 g mixed with 1.6 g mineral oil, 93% yield), which was used without further purification: $C_{15}H_{21}$ $NO_5$ (295.34); $^1$H-NMR ($CDCl_3$) δ8.54 (d,1), 7.65 (m,1), 7.55–7.2 (m,2), 5.34 (s,2), 4.29 (q,2), 3.87 (m,2), 3.59 (m,2), 3.38 (s,3), 2.34 (d,3), 1.38 (t,3).

C. The product of part B (24 g, 81 mmol) was dissolved in 200 ml EtOH and hydrogenated with 10% palladium-on-carbon catalyst (0.75 g) at 1.5 atmospheres for 18 hours. The catalyst was removed by filtration and the filtrate was evaporated to leave ethyl 3-[5-[(2-methoxyethoxy)methoxy] -2-pyridyl]-2-methylpropanoate as a gum.

The gum was dissolved in 1 50 ml dioxane and 150 ml 1N

KOH was added. The mixture was stirred vigorously for 24 hours, poured into water, and extracted with $Et_2O$. The aqueous solution was cooled to 0° C. and the pH was adjusted to 2.5 with 12N HCl. The mixture was suction-filtered to separate the precipitate, and the filtrate was extracted with EtOAc. The precipitate was dissolved with the EtOAc extract. The extract was dried over $Na_2SO_4$, filtered, and evaporated to leave 3-[5-[(2-methoxy-ethoxy)methoxy]-2-pyridyl] -2-methylpropanoic acid.

This product was dissolved in 100 ml THF, 200 ml 1M borane-THF solution were slowly added, then the solution was heated at reflux for 6 hours. The mixture was cooled to room temperature, 40 ml MeOH was added carefully, then 100 ml of 5% aq. $K_2CO_3$ were added and the mixture was stirred vigorously. The mixture was concentrated to ⅓ volume, water was added, and the mixture was extracted with EtOAc. The extract was dried over $Na_2SO_4$, filtered, and evaporated to a residue. The residue was hromatographed on silica gel eluting with EtOAc-hexanes (3:1) to obtain 3-[5-[(2-methoxyethoxy)methoxy]-2-pyridyl]-2-methylpropanol: $C_{13}H_{21}NO_4$ (255.32); $^1$H-NMR ($CDCl_3$) δ8.30 (d,1), 7.35 (dd,1), 7.07 (d,1). 5.28 (s,2), 3.82 (m,2), 3.55 (m,2), 3.39 (s,3), 2.80 (d,2), 2.12 (m,1), 0.94 (d,3).

D. DMSO (4.8 ml. 68 mmol) was added dropwise at −60° C. to a solution of oxalyl chloride (2.8 ml, 32 mmol) in 75 ml $CH_2Cl_2$. A solution of the product of part C (7.6 g, 28 mmol) in 15 ml $CH_2Cl_2$ was then added dropwise at −60° C. After 1 hour at −50° C., 14 ml $Et_3N$ was slowly added, and the mixture was stirred without heating for 4 hours. $Et_2O$ was added, the mixture was suction-filtered, the filtrate was washed with water, dried over $Na_2SO_4$, filtered and evaporated to a residue. The residue was chromatographed on silica gel eluting with EtOAc to obtain 3-[5-[(2-methoxy-ethoxy)methoxy] -2-pyridyl]-2-methylpropionaldehyde (3.8 g, 48% yield): $C_{13}H_{19}NO_4$ MS m/e 253.30; $^1$H-NMR ($CDCl_3$) δ9.84 (s,1), 8.33 (d,l), 7.33(dd,1), 7.08 (d,2), 5.27 (s,2), 3.80 (m,2), 3.55 (m2,), 3.35 (s,3), 3.2–2.6 (m,3), 1.18 (d,3).

E. The product of part D (4.2 g. 17 mmol) was added to a solution of ammonium carbonate (2.75 g, 29 mmol), NaCN (1.0 g, 20 mmol) and 20 ml water. The mixture was stirred and heated at 100° C. for 3 hours, then 12N HCl (approx. 3.8 ml) was added to the hot mixture until the pH was 2–3. The mixture was evaporated to dryness, and the residue was extracted with hot methanol. The methanol was evaporated to leave a residue of crude hydantoin. This residue was dissolved in 20 ml water, 50 g of $Ba(OH)_2.8H_2O$ were added, and the resulting mixture was heated at 110° C. for 18 hours. 250 ml of hot water were added to the mixture and $CO_2$ was bubbled in until precipitation was complete. The mixture was suction-filtered while hot, the filtrate cooled, 12N $H_2SO_4$ was added to adjust the pH 2.5 and and the mixture was suction-filtered again. The filtrate was poured through an AG-50W-X8 ($H^+$) ion exchange column (75 meq), washed with water, then eluted with 1M $NH_4OH$. The basic eluate was evaporated to leave 2-amino -4-[5-[ (2-methoxyethoxy)methoxy]-2-pyridyl]-3-methylbutanoic acid (3.3 g, 67% yield) as a mixture of 4 stereoisomers: $C_{14}H_{22}N_2O_5$ (298.34); ms (FAB) 299 ($M^+$+ 1).

F. $Et_3N$ (6.5 mi, 47 mmol) was added to a solution of the product of part E (3.8 g, 11 mmol) in 75 ml DMF. Then N-(benzyloxycarbonyloxy)succinimide (3.75 g, 15 mmol) was added and the mixture was stirred at room temperature for 20 hours. Most of the solvent was evaporated, 5% aq. citric acid was added, and the mixture was extracted with EtOAc. The extracts were dried over $Na_2SO_4$, filtered, and evaporated to a residue. The residue was chromatographed on silica gel eluting with $CH_2Cl_2$—EtOAc—MeOH—HOAc (300:40:10:1) to obtain 2 diastereomeric pairs of enantiomers of 2-[(benzyloxycarbonyl)amino]-4-[5-[(2-methoxyethoxy)methoxy]- 2-pyridyl]-3-methylbutanoic acid (1.32 g, 27% yield of the first to elute, (±)-(R*,R*)); 1.48 g, 31% yield of the second to elute, (±)-(R*,S*)): $C_{22}H_{28}N_2O_7$ MS m/e (432.48); $^1$H-NMR (indistinguishable, $CDCl_3$) δ8.4 (d,1), 7.7–7.0 (m,2), 7.3 (s,5), 6.1 (d,1 ,NH), 5.3 (s,2), 4.3 (m,2), 3.8 (m,2), 3.5 (m,2), 3.3 (s,3), 3.1-2.4 (m,3), 0.9 (d,3).

G.-1 2,4-dimethoxybenzene (1.49 ml, 3.7 mmol) was added to a solution of the first product of part F to elute (1.35 g, 3.1 mmol) in 24 ml $CH_2Cl_2$. Then trifluoroacetic acid (2.4 ml, 31 mmol) was added and the mixture was stirred for 60 hours. 50 ml xylenes were added and the mixture was evaporated to dryness. The residue was chromatographed on silica gel eluting with $CH_2Cl_2$—EtOAc—MeOH—HOAc (gradient from 300:40:10:1 to 40:40:10:1) to obtain (±)-(R*, R*)- 2-[(benzyloxycarbonyl)amino]-4-(5-hydroxy-2-pyridyl)-3 -methylbutanoic acid (0.94 g, 93% yield): $C_{18}H_{20}N_2O_5$ (344.37); $^1$H-NMR (DMSO-$d_6$) δ8.04 (d,1), 7.71 (d,I,NH), 7.39 (s,5), 7.10 (dd,1), 7.03 (d,1), 5.04 (s,2), 4.00 (dd,1), 2.85–2.45 (m,2), 2.35 (m,1), 0.78 (d,3).

G.-2 The procedure of part G.-1 above was used but the second product of part F was substituted to obtain (±)-(R*, S*)-2-[ (benzyloxycarbonyl)amino)-4-(5-hydroxy-2-pyridyl)-3-methylbutanoic acid (0.88 g, 86% yield): $C_{18}H_{20}N_2O_5$ MS m/e (344.37); $^1$H-NMR (DMSO-$d_6$) δ8.05 (d,1), 7.50 (d,I,NH), 7.36 (s,5), 7.05 (dd,1), 6.96 (d,1), 5.06 (s,2), 3.97 (dd,1), 2.68 (q,1), 2.48 (m2), 0.88 (d,3).

The following table illustrates how compounds of formula I of the invention may be made by using procedures analogous to those set forth above.

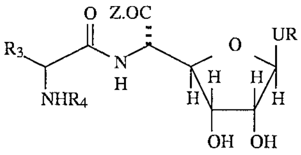

| # | 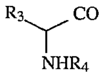 | Z.OC | Starting Materials | Process |
|---|---|---|---|---|
| 1 | 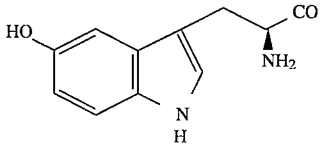 | $CONH(CH_2)_3CH_3$ | Use L-N-BOC-5-hydroxy-Tryptophan in procedure A<br>Use n-butylamine in procedure B | A/B |
| 2 | 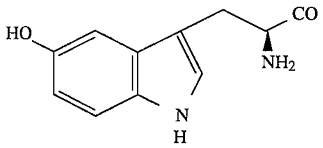 | $CONH(CH_2)_7CH_3$ | Use L-N-BOC-5-hydroxy-tryptophan for procedure A<br>Use n-octylamine in procedure B | A/B |
| 3 | 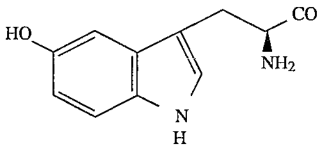 | $CONH(CH_2)_{11}CH_3$ | Procedure given | |
| 4 | 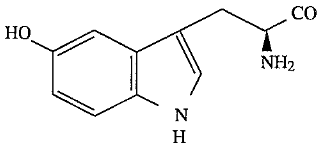 | $CONH(CH_2)_{17}CH_3$ | Use L-N-BOC-5-hydroxy-tryptophan for procedure A<br>use n-octadecylamine in procedure B | A/B |
| 5 | 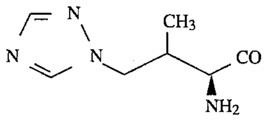 | $CONH(CH_2)_{11}CH_3$ isomer 1 | Use 2-S-N-Fluorinyl-phenylamino3-methyl-4-(1H-1,2,4-triazolyl)-butyric acid in procedure D | C/D |
| 6 | 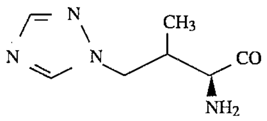 | $CONH(CH_2)_{11}CH_3$ isomer 2 | Use 2-S-N-fluorinylphenyl-isomer 2 amino3-methyl-4-(1H-1,2,4-triazolyl)-butyric acid in procedure D | C/D |
| 7 | 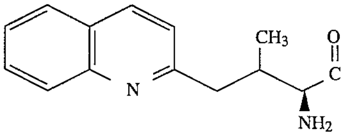 | $CONH(CH_2)_{11}CH_3$ isomer 1 | Use 2-N-BOC-amino-3-methyl-4-(2-quinolinyl)-butyric acid in procedure D. | C/D |
| 8 | 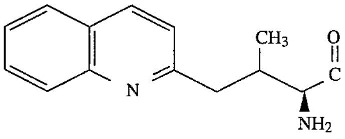 | $CONH(CH_2)_{11}CH_3$ isomer 2 | Use 2-N-BOC-amino-3-methyl-4-(2-quinolinyl)-butyric acid in procedure D. | C/D |
| 9 | 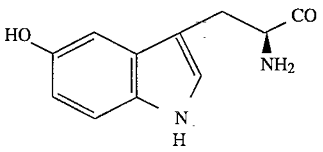 | $CONH(CH_2)_{13}CH_3$ | Use L-N-BOC-5-hydroxy-tryptophan procedure A.<br>Use n-tetradecylamine in procedure B | A/B |

-continued

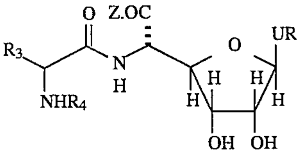

| # | 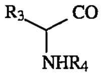 | Z.OC | Starting Materials | Process |
|---|---|---|---|---|
| 10 | 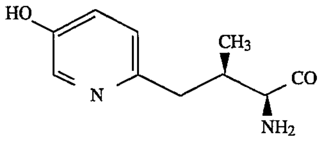 | $CONH(CH_2)_{11}CH_3$ | Use 2-S-N-BOC-amino-3-methyl-4-(5-hydroxypyridyl)-butyric acid in procedure D | C/D |
| 11 | 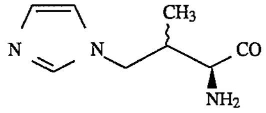 | $CONH(CH_2)_{11}CH_3$ | Use 2-S-N-fluorenylphenyl-amino3-methyl-4-(1H-imidazolyl)-butyric acid in procedure D | C/D |
| 12 | 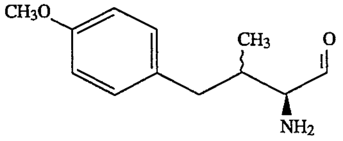 | $CONH(CH_2)_{11}CH_3$ | Use 2-S-N-BOC-amino-3-methyl-4-p-methoxyphenyl-butyric acid in procedure D | C/D |
| 13 | 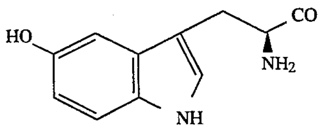 | $CONH(CH_2)_9CH_3$ | Use L-N-BOC-5-Hydroxy-tryptophan in procedure A Use n-decylamine in procedure B | A/B |
| 14 | 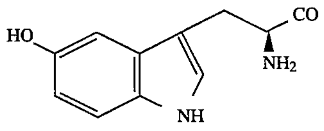 | $CON(OBZL)(CH_2)_{11}CH_3$ | Use L-N-BOC-5-Hydroxy-tryptophan in procedure A. Use benzyloxy-n-dodecylamine in procedure B | A/B |
| 15 | 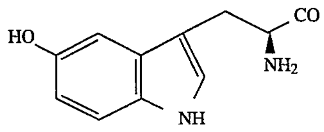 | 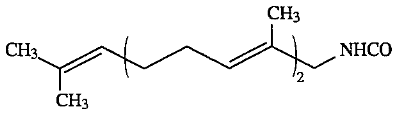 | Use L-N-BOC-5-Hydroxy-tryptophan in procedure C. Use farnesylamine in procedure B | A/B |
| 16 | 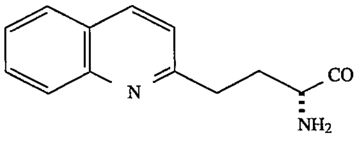 | $CONH(CH_2)_{11}CH_3$ | Use 2-N-BOC-amino-4-(2-quinolinyl)-butyric acid in procedure D | C/D |
| 17 | 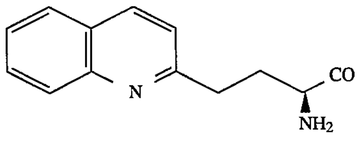 | $CONH(CH_2)_{11}CH_3$ | Use 2-N-BOC-amino-4-(2-quinolinyl)-butyric acid in procedure D | C/D |
| 18 | 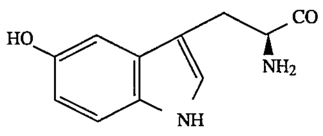 | $CON(OH)(CH_2)_{11}CH_3$ | Use L-N-BOC-5-Hydroxy-tryptophan in procedure C. Hydrogenolyze compound No. 14 above. | A/B |

-continued

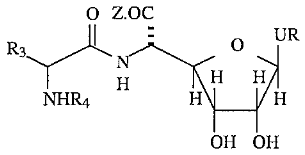

| # | 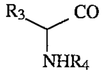 | Z.OC | Starting Materials | Process |
|---|---|---|---|---|
| 19 | 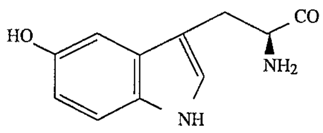 | 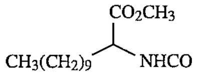 | Use L-N-BOC-5-Hydroxy-tryptophan in procedure C. Use 2-amino-methyl-laurate in procedure B | A/B |
| 20 | 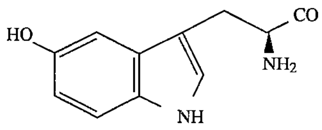 | 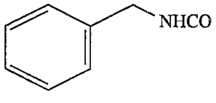 | Use L-N-BOC-5-Hydroxy-tryptophan in procedure C. Use benzylamine in procedure B | A/B |
| 21 | 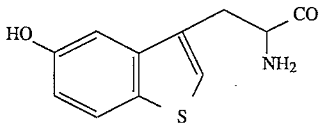 | $CONH(CH_2)_{11}CH_3$ isomer 1 | Use 5-hydroxy-3-(2-N-BOC-amino-propionyl)-benzthiophene in procedure D | C/D |
| 22 | 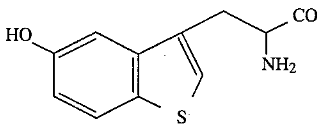 | $CONH(CH_2)_{11}CH_3$ isomer 2 | Use 5-hydroxy-3-(2-N-BOC-amino-propionyl)-benzthiophene in procedure D | C/D |
| 23 | 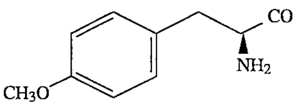 | $CONH(CH_2)_{11}CH_3$ | Use L-methyl-N-BOC-tyrosine in procedure D | C/D |
| 24 | 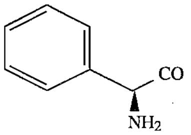 | $CONH(CH_2)_{11}CH_3$ | Use N-BOC-L-phenylglycine in procedure D | C/D |
| 25 | 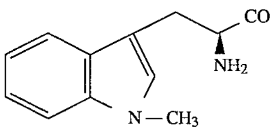 | $CONH(CH_2)_{11}CH_3$ | Use N-methyl-N-BOC-L-tryptophan in procedure D | C/D |

As used in the above table, OBZ means O-benzyl.

What is claimed is:

1. A compound of the formula:

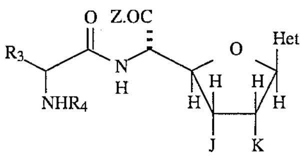

I or pharmaceutically acceptable salts thereof, wherein Het is

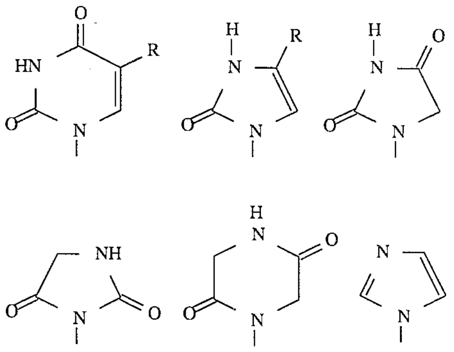

-continued or

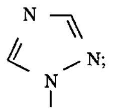

R is H, COOH; $C_1$–$C_{12}$ alkyl; CHO; CN; $CH_2OH$; or $CONH_2$;

wherein $R_3$ is

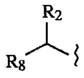

wherein $R_8$ is

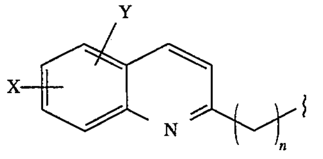

$R_2$ is H; OH; F; $C_1$–$C_6$ alkoxy; alkyl; SH; S-alkyl; or $SO_2$-alkyl;

$R_4$ is H; a natural amino acid attached by a peptide bond; or a metabolizable group;

$R_x$ is $C_1$–$C_{12}$ alkyl;

J is OH, H, Br, Cl, or F;

K is OH, H, Br, Cl, or F;

X and Y are the same or different and are independently selected from the group consisting of H; OH; O—$C_1$–$C_{14}$ alkyl; F; Cl; Br; $NO_2$, and alkyl;

Z is $R_5NR_6$;

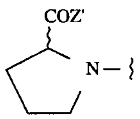 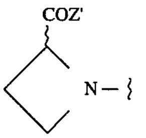 or 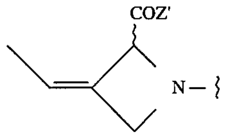

wherein Z' is $R_5NR_6$, $R_5$ is H, a saturated or unsaturated $C_6$–$C_{18}$ aliphatic side chain; or a hydroxylated $C_6$–$C_{18}$ aliphatic side chain;

$R_6$ is H; OH; O-benzyl; O-aryl; O—$C_4$–$C_{14}$ alkyl; $C_1$–$C_{12}$ alkyl; phenyl; substituted phenyl; or CO—$R_7$; and $R_7$ is H, $C_1$–$C_{16}$ alkyl, aryl or alkylaryl; and n is an integer from 0 to 16.

2. A compound according to claim 1 wherein Het is uracil.

3. A compound according to claim 1 wherein $R_4$ is H.

4. A compound according to claim 3, wherein $R_5$ is $(CH_2)_{11}CH_3$.

5. A compound according to claim 1, wherein J and K are both OH.

6. A compound according to claim 1, selected from the group consisting of

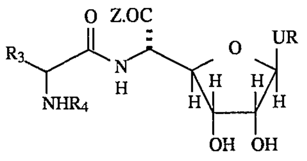

wherein:

| No. | 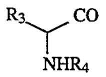 | Z.OC |
|---|---|---|
| 7. | 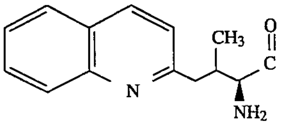 | $CONH(CH_2)_{11}CH_3$ isomer 1 |
| 8. | 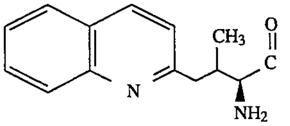 | $CONH(CH_2)_{11}CH_3$ isomer 2 |
| 16. | 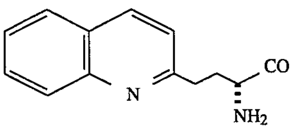 | $CONH(CH_2)_{11}CH_3$ |
| 17. | 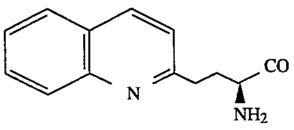 | $CONH(CH_2)_{11}CH_3$ |

or a pharmaceutically acceptable salt of such a compound.

7. The compound according to claim 1,

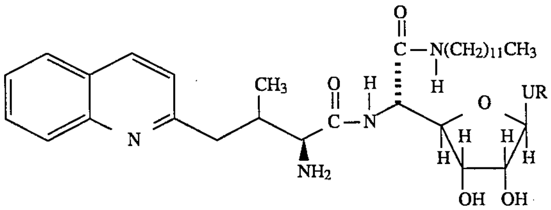

or a pharmaceutically acceptable salt thereof.

8. A pharmaceutical composition comprising a compound according to claim 1 in combination with a pharmaceutically acceptable carrier.

9. A method for treating a fungal infection in a mammal which comprises administering to the mammal an antifungally effective amount of a compound according to claim 1.

* * * * *